US006967257B1

(12) United States Patent
Van Krieken et al.

(10) Patent No.: US 6,967,257 B1
(45) Date of Patent: Nov. 22, 2005

(54) METHOD OF PURIFYING LACTIC ACID ESTERS

(75) Inventors: Jan Van Krieken, Gorinchem (NL); Johannes Jeichinus De Vries, Dalem (NL); Symone Kok, Giessenburg (NL)

(73) Assignee: Purac Biochem B.V., (NL)

( * ) Notice: Subject to any disclaimer, the term of this patent is extended or adjusted under 35 U.S.C. 154(b) by 0 days.

(21) Appl. No.: 10/149,652

(22) PCT Filed: Nov. 24, 2000

(86) PCT No.: PCT/NL00/00860

§ 371 (c)(1),
(2), (4) Date: Sep. 18, 2002

(87) PCT Pub. No.: WO01/44157

PCT Pub. Date: Jun. 21, 2001

(30) Foreign Application Priority Data

Dec. 16, 1999 (NL) .................................. 1013870

(51) Int. Cl.⁷ ..................... C07C 69/66; C07C 51/42

(52) U.S. Cl. ..................................... 560/179; 562/580
(58) Field of Search ..................... 562/580; 560/179

(56) References Cited

U.S. PATENT DOCUMENTS 5,264,592 A * 11/1993 Fridman et al.
6,310,218 B1 * 10/2001 O'Brien et al.

OTHER PUBLICATIONS

Patent Abstracts of Japan, vol. 01, No. 1202 (C-432), Jun. 30, 1987.

* cited by examiner

*Primary Examiner*—Cecilia J. Tsang
*Assistant Examiner*—Taylor Victor Oh
(74) *Attorney, Agent, or Firm*—Gilberto M. Villacorta

(57) ABSTRACT

The invention relates to a method of purifying lactic acid esters, wherein an impure lactic acid ester is subjected to a melt crystallization. The impure lactic acid contains not more than 10 wt. % of impurities, based on the total amount of ester, and has a chiral purity of more than 90%. The ester is derived from lactic acid and a $C_1$–$C_{18}$ alcohol.

4 Claims, No Drawings

METHOD OF PURIFYING LACTIC ACID ESTERS

The invention relates to a method of purifying lactic acid esters. In particular, the invention relates to the purification of lactic acid esters on an industrial scale.

The prior art discloses various methods of purifying esters of lactic acid. The American U.S. Pat. No. 5,571,657, published on 5 Nov. 1996, describes a method of removing metal ions from organic solvents for, and solutions of, photoetching components, which involves brining the solvent, for example a mixture of ethyl lactate and butyl acetate, into contact with a cationogenic exchange resin. Neither crystalline lactic acid esters not pure enantiomers thereof are described.

The Japanese Patent Application 8208565, published on 13 Aug. 1996, describes a method which involves the preparation of ethyl lactate by reacting lactic acid with ethanol in the presence of a catalyst such as p-toluenesulphonic acid, after which the ethyl lactate is worked up and is then purified by means of distillation. Neither crystalline lactic acid esters not pure enantiomers thereof are described.

The Japanese Patent Application 8012621, published on 16 Jan. 1996, describes a method in the course of which a lactic acid ester obtained from a fermentation process is treated with activated carbon and then distilled in order to lower its UV absorption at a wavelength of 300 nm or less. The product obtained has a UV absorption at 280 nm of 1 or less, a purity of at least 99.5% and a metal level of at most 10 ppb. Crystalline lactic acid esters are not described.

JP A 62026249 (published on 4 Feb. 1987) describes a method of obtaining lactic acid esters in pure form, which involves adjustment of the pH of the impure ester to a value of from 6 to 8.5 and subsequent distillation of the impure ester. Crystalline lactic acid esters are not described.

Applicant's experience has shown that the known methods allow only inadequate purification of esters of lactic acid. Thus the by-product acetic acid generally proves to be very difficult to separate from ethyl lactate, which means that too much free acid is present in the ester. Moreover, the colour of the distilled ester is often found not to satisfy the requirements posed. Other impurities too, such as pyruvic acid esters cannot readily be removed by distillation. Nor can such problems be solved by the use of activated carbon. Moreover, in practice it is particularly important to be above to provide a lactic acid ester of constant quality, i.e. that during production the ester always meets specifications such as free-acid content and colour and that the ester is stable.

The Beilstein database predominantly reports melting points of racemic mixtures of lactic acid ester. These melting points are often lower than those of the corresponding pure enantiomers.

It is an object of the invention to provide a solution to the above-described problems. The invention therefore relates to a method of purifying lactic acid esters, wherein an impure lactic acid ester is subjected to a melt crystallization.

Melt crystallization is a process in which a crystalline material is obtained from a melt of the material to be crystallized. This technique is described in detail, for example, in Kirk-Othmer, Encyclopedia of Chemical Technology, fourth edition, Volume 7, pp. 723–727 (1993), in J. W. Mullin, "Crystallization", third revised edition, Butterworth-Heinemann Ltd, pp. 309–323 (1993) and in J. Ullrich and B. Kallies, Current Topics in Crystal Growth Research, 1 (1994), which are incorporated for reference. The major advantage of melt crystallization compared with distillation is that much less energy is required, as the enthalpy of fusion of organic compounds is generally lower than the enthalpy of evaporation. A further advantage of melt crystallization compared with distillation is that the process can generally be carried out at a much lower temperature, which is advantageous if the organic compound is thermally unstable.

Surprisingly it was found that lactic acid esters can be purified in a particular suitable manner by subjecting them to a melt crystallization. The impure lactic acid ester preferably contains not more than 10 wt % impurities, based on the total amount of ester and in particular not more than 2 wt % of impurities.

According to the invention, the impure acid esters have a chiral purity of more than 90% and in particular more than 98 wt %. Chiral purity is defined here as:

Chiral purity=100%×{(R-isomer)/(R-isomer+S-isomer)}

The purified esters have a purity of at least 98 wt %, preferably at least 99.5 wt % and in particular at least 99.9 wt %, based on the total amount of ester. Furthermore, the purified esters have a free-acid content of at most 0.2%, preferably at most 0.05% and in particular not more than 0.02%. The colour of the purified esters is preferably not more than 20 APHA units and in particular not more than 5 APHA units. The water content of the ester is preferably not higher than 0.2 wt % and in particular not higher than 0.05 wt %, based on the total amount of ester.

The esters can have been prepared from lactic acid obtained by fermentation or form a stereoselective esterification of racemic lactic acid. The method according to the present invention is suitable for esters having only low chiral purity. The method according to the invention however, is suitable, in particular, for substantially chirally pure esters.

The esters are preferably derived from lactic acid and a $C_1$–$C_{18}$ alcohol. Preferably, these alcohols are linear, branched and/or cyclic alkanols or alkenols, aryl- or heteroarylalkylalkanols, or tetrahydrofuryl-, tetrahydrothienyl- or pyrrolidinyl- alkanols, where the alkanols or alkenols can carry alkoxy group or alkenoxy group substituents. Examples of suitable esters are methyl lactate, ethyl lactate, n-propyl and isopropyl lactate, n-butyl, isobutyl and t-butyl lactate, n-pentyl and isopentyl lactate, neopentyl lactate, n-hexyl, 2-ethylexyl, cyclohexyl, cis-3-hexenyl, n-heptyl, isoheptyl, n-octyl, n-nonyl, isononyl, n-decyl, n-undecyl, n-dodecyl, n-tridecyl, isotridecyl, benzyl, tetrahydrofuryl, allyl, menthyl, myristyl, cetyl and stearyl lactate. Examples of esters having alkoxy groups are 2-butoxyethyl lactate and 2-ethoxyethyl lactate.

The esters can also be diesters such as 1,2-propylene glycol dilactate or esters derived from diols, triols and polyols, in which one or more hydroxyl groups are esterified with lactic acid. Examples of such compounds are glycerol monolactate, 1,2-propylene glycol monolactate, dipropylene glycol monomethyl ether lactate and propylene glycol monomethyl ether lactate.

The melt crystallization can be carried out with the aid of a suspension crystallization or a layer crystallization, possibly in combination with a wash column or a centrifuge, or some other purification technique. Examples of suitable apparatuses and processes are described in Kirk-Othmer, Encyclopedia of Chemical Technology, fourth edition, Volume 7 pp. 723–727 (1993), in J. W. Mullin, "Crystallization", third revised edition, Butterworth-Heinemann Ltd., pp. 309–323 (1993) and J. Ullrich and B. Kallies, Current Topics in Crystal Growth Research, 1 (1994), whose contents are incorporated by reference.

the lactic acid esters purified in accordance with the method according to the invention are suitable, in particular, for use in electronics, stereoselective syntheses of chemical compounds (see, e.g. DE-A-3 902 372, GB-2 005 668, De-A-3 638 119, U.S. Pat. No. 4,940,813, U.S. Pat. No. 5,814,433 and EP-A-442 952).

The invention will now be explained with reference to the following examples.

EXAMPLE 1

In a three-neck round-bottom flask, 400 ml of ethyl (S)-lactate (free-acid content [measured as lactic acid] 1.13 wt %, GLC purity 99.39%, 0.29 wt % of acetic acid, chiral purity 98.00%) were cooled slowly with stirring to −6° C. Crystallization commenced at −5° C. After a few hours the crystals were separated off with the aid of a laboratory basket centrifuge (type Sieva from Hermle). The yield was 6%, based on the initial amount. After melting, the purity was determined: GLC purity 99.96%, 0.00% of acetic acid, chiral purity 99.99%.

EXAMPLE 2

Isobutyl (R)-lactate (500 ml, chiral purity 95.4%) was stored at −20° C. for two days. A block of solid product was obtained. The block of solid product was warmed slowly at ambient temperature, a fraction of the solid product liquefying in the process. The remaining fractions were loosened with the aid of a spatula, affording a readily stirrable suspension. The suspension was separated in a laboratory basket centrifuge, and the isolated crystals were melted by letting them stand at ambient temperature. From a suspension of 445 g, 126 g of crystals were obtained. The chiral purity of the product obtained was 99.85%.

EXAMPLE 3

A quantity of 40 kg of ethyl lactate (free-acid content [measured as lactic acid] 0.12 wt %, water content 0.42 wt %, GLC purity 99.56%, 0.19 wt % of ethyl 2-hydroxybutanoate) was crystallized in an industrial melt crystallization pilot set-up. Analysis of the product gave the following results: free acid content <0.001%, water content 0.02%, GLC purity 99.98%, 0.02 wt % of ethyl 2-hydroxybutanoate, chiral purity <99.9%).

EXAMPLE 4

The table below gives the melting points of a few esters.

| Lactic acid ester | Melting point (° C.) |
| --- | --- |
| Methyl (S)-lactate | −44 |
| Ethyl (S)-lactate | −3 |
| Propyl (S)-lactate | −14 |
| Isopropyl (S)-lactate | 3 |
| Butyl (S)-lactate | −15 |
| Isobutyl (S)-lactate | 1 |
| 2-Ethylhexyl (S)-lactate | −23 |
| Octyl (S)-lactate | −8 |
| Lauryl (S)-lactate | 25 |

As (chirally+chemically) pure a sample as possible of the ester is cooled until it is one solid block. Then the sample is slowly warmed and loosened. Once a readily stirrable suspension has been obtained, the temperature is read off and is noted down as the melting point.

What is claimed is:

1. A method of purifying optically active lactic acid esters, comprising the step of subjecting an impure optically active lactic acid ester having a melting point ranging from about 25° C. to about −44° C. to a melt crystallization.

2. The method according to claim 1, wherein the impure ester contains not more than 10 wt % of impurities, based on the total amount of ester.

3. The method according to claim 1, wherein the impure ester has a chiral purity of more than 90%.

4. The method according to claim 1, wherein the impure ester is derived from lactic acid and a $C_1$–$C_{18}$ alcohol.

* * * * *